United States Patent [19]

Yamaguchi et al.

[11] Patent Number: 5,502,215
[45] Date of Patent: Mar. 26, 1996

[54] METHOD FOR PURIFICATION OF LACTIDE

[75] Inventors: Yoshiaki Yamaguchi, Tokyo; Tomohiro Arimura, Kanagawa, both of Japan

[73] Assignee: Musashino Chemical Laboratory, Ltd., Tokyo, Japan

[21] Appl. No.: 348,305

[22] Filed: Dec. 2, 1994

[30] Foreign Application Priority Data

Dec. 8, 1993 [JP] Japan .................................. 5-308346

[51] Int. Cl.$^6$ ................................................ C07D 319/12
[52] U.S. Cl. .................................................... 549/274
[58] Field of Search ............................................. 549/274

[56] References Cited

FOREIGN PATENT DOCUMENTS 4022257 7/1990 Germany .
9200974 6/1991 WIPO .

*Primary Examiner*—C. Warren Ivy
*Assistant Examiner*—Amelia Owens
*Attorney, Agent, or Firm*—Gordon W. Hueschen

[57] ABSTRACT

A method for the purification of lactide is provided which permits lactide of high optical purity or DL-lactide of high purity to be produced from crude lactide by the removal of meso-lactide from the crude lactide. This method for the purification of lactide is characterized by causing a mixture containing L-lactide and/or D-lactide together with meso-lactide to contact with water thereby effecting hydrolysis of meso-lactide. This method can remove meso-lactide from crude lactide and produce DL-lactide and/or optically active lactide of high optical purity in high yield and, in the production of optically active lactide, can eliminate the restrictions otherwise imposed on the formation of meso-lactide. Thus, it lends itself to the simplification of the procedure for the synthesis of lactide.

6 Claims, 1 Drawing Sheet

FIGURE
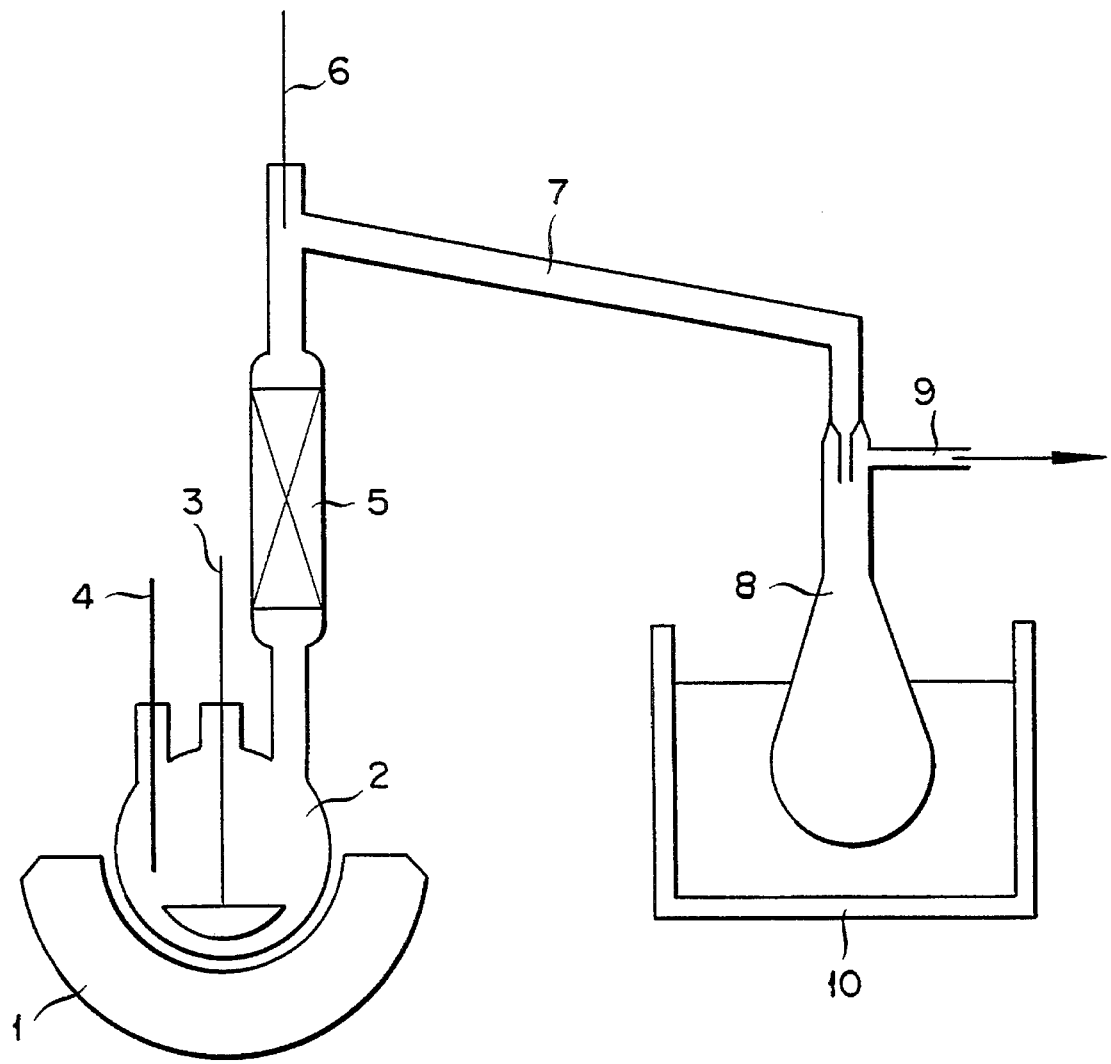

METHOD FOR PURIFICATION OF LACTIDE

BACKGROUND OF THE INVENTION

1. Field of the Invention

This invention relates to a method for the purification of lactide which is a cyclic ester formed from two molecules of lactic acid.

2. Description of the Prior Art

Lactide which is a cyclic ester formed from two molecules of lactic acid has been known to have three forms; L-lactide molecule formed from two molecules of L-lactic acid, D-lactide molecule formed from two molecules of D-lactic acid, and meso-lactide molecule formed from L-lactic acid and D-lactic acid.

Lactide is an important compound as an intermediate for polylactic acid which has been attracting attention as a biodegradable plastic substance in recent years. It has been known that polylactic acid with a high molecular weight can be obtained by the ring-opening polymerization of lactide.

The nature of the polylactic acid is varied by the optical purity of the lactic acid monomer forming the polylactic acid, namely the optical purity of the polylactic acid, as well as by the molecular weight of the polylactic acid. It has been known that pure L- or D-polylactic acid excels L- or D-polylactic acid having a like molecular weight and a lower optical purity in terms of strength or formability. Perfect racemic lactic acid, namely, DL-polylactic acid formed from DL-lactic acid, excels optically active polylactic acid in terms of flexibility and, therefore, is expected to find utility in special applications.

Now, the methods heretofore introduced to the art for the synthesis of lactide will be described below.

Lactide is generally synthesized by the so-called reaction distillation method which uses polylactic acid with a relatively low molecular weight (lactic acid oligomer which will be referred to hereinafter as "prepolymer" in association with the reaction for synthesis of lactide) as an intermediate and which comprises the steps of cyclizing this intermediate at a temperature of not lower than 180° C. in the presence of a catalyst thereby forming lactide which is a cyclic ester formed from two molecules of lactic acid and extracting this lactide in the form of vapor out of the reaction system. To be more specific, the lactide is synthesized by the following procedure using lactic acid as a raw material.

(1) Lactic acid is heated under a reduced pressure (generally below 20 mmHg) until dehydration and condensation thereof and converted into a prepolymer. The temperature of this heating is kept below 180° C. for the purpose of preventing lactic acid from racemization.

(2) The prepolymer and SnO added thereto as a catalyst for the synthesis of lactide are together heated under a reduced pressure and left reacting at a temperature in the approximate range of 180° to 230° C. while removing the formed lactide vapor by distillation.

(3) The lactide vapor is cooled and collected. It is recovered in a liquid state at a temperature exceeding 60° to 90° C. lest it should condense.

In the dehydration and condensation of lactic acid at the step (1) mentioned above, the reaction part may preparatorily contain the catalyst for the synthesis of lactide at the step (2). The idea of adapting the steps (1) to (3) of the procedure mentioned above to proceed as a continuous operation carried out and consequently exalting the efficiency of synthesis constitutes a naturally conceived method.

The lactide vapor expelled by distillation from the reaction part for the synthesis of lactide at any of the steps mentioned above contains lactic acid monomer, lactic acid dimer (lactoyllactic acid), and water as impurities. Hereinafter, the lactide which contains these impurities will be referred to as "crude lactide".

Of these impurities, the lactic acid monomer and the lactic acid dimer are acid components. During the synthesis of the polylactic acid by the ring-opening polymerization of lactide, therefore, they inconvenience the severance of the polylactic acid chain and the consequent production of polylactic acid with a high molecular weight. The presence of water promotes the hydrolysis of polylactic acid or lactide and entails the formation of an acid component and, as a result, similarly inconveniences the production of polylactic acid having a high molecular weight.

Generally, these impurities are removed from the crude lactide by such a method as crystallization, extraction, or distillation to permit the production of purified lactide.

When the separation of lactide from these impurities is effected by ordinary crystallization, however, the yield by the crystallization is too low to be commercially acceptable satisfactorily for the production of lactide of high purity.

In the separation by distillation, lactic acid and lactide undergo thermal polymerization, hydrolysis, etc. during the course of distillation. Since their thorough separation is difficult and the yield of lactide is low, this method does not deserve to be rated as satisfactory.

The method disclosed in WO 92/00974 which comprises the steps of dissolving crude lactide in such a solvent as acetone which is compatible with water, adding cold water to the resultant solution thereby inducing crystallization of lactide, and separating the lactide crystals from the other components of the reaction solution is claimed to produce lactide of high purity. This method suffers from heavy loss due to the crystallization because the solubility of lactide in acetone is high. It has been already known to remove the acid components from the crude lactide by dissolving the crude lactide in a solvent incompatible with water and exposing the resultant solution to contact with water thereby inducing extraction of the acid components from the solution. This method, however, permits no sufficient separation of L-lactide or D-lactide from meso-lactide.

When L-form optically active lactic acid is used as the raw material for the crude lactide, the lactic acid inevitably undergoes racemization and gives rise to meso-lactide and a minute amount of D-lactide in addition to L-lactide because an amply high reaction temperature and an amply long retention time must be used generally for allowing the reaction to proceed fully.

When DL-lactic acid is used as the raw material for the crude lactide, it only naturally follows that the reaction produces meso-lactide in addition to DL-lactide which is an equivalent mixture of D-lactide and L-lactide.

For the purpose of synthesizing polylactic acid with a high molecular weight and having a high optical purity, it is necessary that the lactic acids which are components of the lactide being used as the raw material possess a high optical purity, namely the lactide itself possess a high optical purity.

Further, in the synthesis of DL-polylactic acid, the lactide as the raw material therefor is an equivalent mixture of L-lactide and D-lactide. It may contain meso-lactide without posing any problem from the compositional point of view. When lactide in a solid state is handled as an intermediate raw material, however, the solid lactide is so soluble as to impair the convenience of the handling thereof because meso-lactide has high hygroscopicity and a low melting point in the approximate range of 40° to 42° C.

In view of the various factors remarked above, it is desired in the manufacture of lactide to obtain lactide containing no meso-lactide. With respect to a measure to remove meso-lactide from lactide, no appreciable study has been heretofore made.

SUMMARY OF THE INVENTION

The present inventors continued a diligent study with a view to solving the problems mentioned above and obtaining lactide of high optical purity aimed at from the crude lactide, namely obtaining DL-lactide of high purity by removing meso-lactide. As a result of the study, they have remarked that meso-lactide is dissolved faster in water and hydrolyzed faster therein than L-lactide or D-lactide and that L-lactide or D-lactide manifests very low solubility in cold water and eventually found that by keeping crude lactide in contact with water for a prescribed time, meso-lactide is efficiently removed from the crude lactide because the meso-lactide preferentially passes into the water phase and dissolves therein and part of the meso-lactide even undergoes hydrolysis. They have demonstrated that the lactide obtained as described above entrains such impurities as meso-lactide, lactic acid and other acid components only in a small amount and, therefore, can be purified simply. The present invention has been perfected as a result.

The object of this invention is accomplished by (1) a method for the purification of lactide characterized by removing meso-lactide from a mixture containing at least one lactide selected from the group consisting of L-lactide and D-lactide together with meso-lactide by causing the mixture to contact with water.

The object of this invention, when the content of meso-lactide in the crude lactide is relatively small, is accomplished by (2) a method for the purification of lactide characterized by removing meso-lactide from a mixture containing at least one lactide selected from the group consisting of L-lactide and D-lactide together with meso-lactide and existing in a molten state and, at the same time, inducing separation in the form of crystals of at least one lactide selected from the group consisting of L-lactide and D-lactide by causing the mixture to contact with water.

The object of this invention, when the content of meso-lactide in the crude lactide is relatively large, is accomplished by (3) a method for the purification of lactide characterized by removing meso-lactide from a mixture containing at least one lactide selected from the group consisting of L-lactide and D-lactide together with meso-lactide and at least partly existing in a molten state and, at the same time, inducing separation in the form of crystals of at least one lactide selected from the group consisting of L-lactide and D-lactide by causing the mixture to contact with water.

The object of this invention is further accomplished by (4) a method for the purification of lactide according to any of the items (1) to (3) mentioned above, wherein the mixture containing at least one lactide selected from the group consisting of L-lactide and D-lactide together with meso-lactide contains lactic acid, water, and other impurities.

The object of this invention is also accomplished by (5) a method for the purification of lactide characterized by dissolving the crystals of L-lactide and/or D-lactic obtained by the method of any of the items (1) to (4) mentioned above in a solvent incapable of reacting with lactide and subjecting the solution to recrystallization.

Incidentally, the expression "L-lactide and/or D-lactide" as used in this invention refers to any one member selected from the group consisting of L-lactide, D-lactide, and a mixture thereof and this term "mixture" embraces DL-lactide, i.e. an equimolar mixture of L-lactide and D-lactide, as a racemic modification.

The method of this invention for the purification of lactide can produce DL-lactide and/or optically active lactide of high optical purity in a high yield from the crude lactide synthesized by the conventional method by removing meso-lactide from the crude lactide.

In the production of optically active lactide according to this invention, the method for synthesis of lactide can be simplified because the restrictions otherwise imposed on the formation of meso-lactide in the reaction distillation part for the synthesis of optically active lactide are eliminated and the conditions for the operation of the reaction distillation part are allowed to be freely set.

Even when the molecular weight of the prepolymer as an intermediate is heightened in order to decrease the lactic acid monomer content in the crude lactide and exalt the yield of lactide, the meso-lactide which is formed in a relatively large amount in consequence of the racemization due to the elongation of the retention time in the reaction part can be removed readily and the heretofore hardly attainable production of lactide of high optical purity in a high yield as a whole can be realized by adopting the method of this invention.

BRIEF DESCRIPTION OF THE DRAWING

FIG. 1 is a diagram illustrating an experimental apparatus for the production of crude lactide from a prepolymer by reaction distillation.

EXPLANATION OF THE PREFERRED EMBODIMENT

Now, the method of this invention will be explained in detail below.

The dehydration and condensation of lactic acid which precedes the reaction for the synthesis of lactide is generally carried out at a temperature in the approximate range of 160° to 180° C. under a reduced pressure to synthesize a prepolymer having an average molecular weight in the approximate range of 400 to 3,000.

Then, the synthesis of lactide is implemented by combining the prepolymer mentioned above with a catalyst selected from among such metals as tin, zinc, lead, iron, antimony, magnesium, and titanium in a powdery form, organic acid salts and inorganic acid salts of the aforementioned metals, metal oxides, and alkyl metals, cyclizing the resultant mixture as stirred under a pressure of not more than 20 mmHg at a temperature in the range of 180° to 230° C., distilling the product of cyclization thereby extracting the formed crude lactide in the form of vapor, and recovering the extracted crude lactide in a liquid state at a temperature in the range of 70° to 110° C.

The composition of the crude lactide thus recovered is widely varied by the reaction temperature and pressure, the retention time in the reaction part, the molecular weight of the prepolymer, the kind and quantity of the catalyst, etc. The composition of the crude lactide produced from L-lactic acid as a raw material generally falls within the ranges as shown in Table 1 below.

TABLE 1

| Composition of crude lactide | Composition ratio (wt %) |
| --- | --- |
| L-lactide | 70–90 |
| D-lactide | <1 |
| Meso-lactide | 3–25 |
| Lactic acid monomer | 2–10 |
| Lactic acid dimer | 2–10 |
| Water | 0.1–5 |

Then, the composition of the crude lactide produced from DL-lactic acid as a raw material generally falls within the ranges as shown in Table 2 below.

TABLE 2

| Composition of crude lactide | Composition ratio (wt %) |
| --- | --- |
| DL-lactide | 40–55 |
| Meso-lactide | 35–40 |
| Lactic acid monomer | 5–20 |
| Lactic acid dimer | 5–20 |
| Water | 0.1–5 |

In order for this lactide to be used for the synthesis of polylactic acid with a high molecular weight, it is necessary that water and acid components be removed from the crude lactide. This removal can be substantially accomplished by such means as crystallization, extraction, or distillation.

In the production of optically active lactide from L-lactic acid or D-lactic acid as a raw material, it is also necessary that meso-lactide be separated. When the amount of meso-lactide to be removed is small, the meso-lactide can be removed to a certain degree by such means as crystallization, extraction, or distillation. If the ratio of meso-lactide to L-lactide and/or D-lactide is unduly large, the separation of meso-lactide will not be satisfactorily attained by the above-mentioned means.

The crystallization is a highly suitable measure to remove a minute amount of impurities. If the proportion of meso-lactide is larger than 3 to 4% by weight, the yield of L-lactide and/or D-lactide by crystallization will not be obtained satisfactorily.

In the extraction which is effected, for example, by a procedure comprising the steps of dissolving crude lactide in an organic solvent incapable of thoroughly mixed with water and contacting the resultant solution with water thereby extracting acid components, namely monomer, dimer, etc. of lactic acid in the water phase, hydrolysis of meso-lactide can occur because meso-lactide and L-lactide and D-lactide pass slightly into the water phase. If the meso-lactide content in the crude lactide is high, however, no fully satisfactory removal will be obtained. Particularly, such a short time that is enough for the extraction of acid components, namely monomer, dimer, etc. of lactic acid is not sufficient for the purpose of hydrolyzing meso-lactide.

The separation by distillation, though theoretically conceivable, entails a difficult operation and necessitates a large number of process steps. Particularly when the crude lactide containing water and acid components is distilled to effect the separation of meso-lactide from the crude lactide, the distillation is at a disadvantage in entailing such reactions as thermal polymerization of lactide in the distillation vessel and degrading the yield.

Then, in the reaction distillation using DL-lactic acid as a raw material, it is only self-evident that the measure of crystallization or extraction mentioned above is absolutely incapable of discharging its function in the attempted separation of meso-lactide from the distilled crude lactide because the ratio of meso-lactide to DL-lactide is appreciably large. The distillation has the same problem as is encountered when the optically active lactide is to be obtained as described above.

By the methods of separation heretofore known to the art, it is difficult to attain effective removal of meso-lactide from the crude lactide as remarked above.

The present inventors have firstly taken notice of the differences between the physical properties of L-lactide, D-lactide, and meso-lactide, then found that the solubility speed of each lactide in water and the speed of hydrolysis thereof are significantly different to each other, and finally perfected this invention by applying the significant differences mentioned above to the separation of meso-lactide.

For example, the solubility speeds of L-lactide, D-lactide, and DL-lactide in consequence of hydrolysis in 100 g of water are in the range of 0.5 to 0.6 g/hr at 20° C. and in the range of 4 to 5 g/hr at 60° C. Under the same conditions, 10 g of meso-lactide is dissolved within one minute and then hydrolyzed gradually.

When the crude lactide and water are held in contact with each other at a relatively low temperature for a prescribed time, therefore, meso-lactide is dissolved in water and, at the same time, partially hydrolyzed therein preferentially over L-lactide and D-lactide. Thus, the meso-lactide can be readily removed in conjunction with such impurities as lactic acid monomer, i.e. another acid component.

This invention can be embodied in various manners, depending on the composition of the crude lactide to be handled.

Now, a few of the conceivable embodiments of this invention will be explained in detail below. They are simply examples selected from various embodiments and are not meant to limit the scope of this invention.

When L-lactic acid is used as a raw material, the temperature of the crude lactide is kept in the vicinity of 90° C. because the crude lactide has a high L-lactide content. When the molten crude lactide is mixed with a substantially equal weight of water and the resultant mixture is immediately cooled to below 30° C. for the purpose of preventing L-lactide from undergoing hydrolysis, the greater part of L-lactide in the mixture is separated in the form of crystals and the mixture is made to assume a slurry state. When the slurry mixture containing L-lactide crystals is kept at 30° C. and stirred for a period in the range of 10 to 30 minutes, the greater part of meso-lactide in the crude lactide is dissolved in water and, at the same time, part of the dissolved meso-lactide is hydrolyzed and, as a result, removed from the crude lactide. The L-lactide crystals are separated by filtration from the water phase and are then dissolved in such an organic solvent as acetone or methyl isobutyl ketone (MIBK) thereby recrystallizing therefrom to produce readily L-lactide crystals of high purity and high optical purity.

When DL-lactic acid is used as a raw material, the crude lactide has a high meso-lactide content. When the crude lactide is gradually cooled, DL-lactide is precipitated and allowed to persist in the form of crystals in the molten meso-lactide phase and the whole crude lactide assumes a slurry state. The crude lactide in the slurry state is mixed with a substantially equal weight of water and the resultant mixture is immediately cooled to the vicinity of 30° C. for the purpose of preventing DL-lactide from undergoing hydrolysis and kept stirred at this temperature for a period in the range of 30 minutes to one hour, with the result that meso-lactide is dissolved in water and, at the same time, part of the dissolved meso-lactide undergoes hydrolysis. The crystals of DL-lactide are separated by filtration from the water phase and are dissolved in such an organic solvent as acetone or MIBK thereby recrystallizing therefrom to produce easily DL-lactide crystals of high purity.

Thus, in the case of DL-lactide, since DL-lactide has a melting point widely different from the melting point of meso-lactide, the method described above is advantageous over the method resorting to direct contact of the molten crude lactide with water in the sense that it permits repression of the loss of DL-lactide.

The duration of the contact between the crude lactide and water and the temperature of the hydrolysis do not need to be limited to the specific ranges remarked in the embodiment described above but may be set suitably as occasion demands. If the temperature exceeds 60° C., however, the operation aimed at improving the yield will be implemented only with difficulty because the speeds of hydrolysis of L-lactide and D-lactide are inevitably heightened notwithstanding the speed of hydrolysis of meso-lactide is improved as desired.

Though no particular restriction is imposed on the manner in which the mixture mentioned above is to be effected, a method which comprises continuously feeding the crude lactide and water to a reaction vessel and mixing them therein, immediately cooling the resultant mixture to a prescribed temperature, and allowing the cooled mixture to stand at the temperature for a prescribed period, a method which comprises preparing the mixture batchwisely, cooling the mixture to a prescribed temperature within a prescribed duration, and allowing the cooled mixture to stand at the temperature for a prescribed period, a method which comprises gradually feeding the crude lactide to water controlled at a prescribed temperature thereby inducing growth of crystals of L-lactide and D-lactide, and a method which comprises preparing the crude lactide in a solid state, pulverizing the solid crude lactide and causing the pulverized crude lactide to contact with water may be cited as measures available for the mixing under discussion.

The "water" which is usable for this invention basically has no particular restriction so long as the solubility speed and the speed of hydrolysis of meso-lactide therein are higher than those of L-lactide and/or D-lactide and the solubilities of L-lactide and/or D-lactide therein are sufficiently low. In view of this definition, the term "water" as used in this invention embraces aqueous solutions which have dissolved therein such substances as water-soluble solvents.

As concrete examples of the impurities which are entrained in the mixture comprising L-lactide and/or D-lactide and meso-lactide for the use in this invention, lactic acid, water, and other impurities may be cited. In these impurities, the lactic acid embraces D-lactic acid, L-lactic acid, and a mixture thereof (inclusive of DL-lactic acid) which constitute the lactic acid monomer used as a raw material. The term "water" as used herein exclusively means pure water ($H_2O$) and does not embrace the water in the broad sense of the word remarked above. The term "other impurities" embraces those impurities as are included in the raw material besides the lactic acid dimer.

The method of this invention for the purification of lactide is a measure effective in obtaining DL-lactide from the crude lactide synthesized by the conventional method by the removal of meso-lactide from the crude lactide and is also a measure suitable for obtaining lactide of high optical purity in high yield in the production of optically active lactide. Further, particularly in the production of optically active lactide, the usefulness of this method can be stressed in respect that it lends itself to the simplification of the procedure for the synthesis of lactide.

The method for the synthesis of lactide has been already described. When the optically active lactide is to be produced by using as an optically active lactic acid the lactic acid destined to constitute the raw material for the prepolymer which is an intermediate, the crude lactide contains by-produced acid components and meso-lactide. In the production of lactide having particularly high optical purity, it is necessary that the meso-lactide content of the crude lactide be lowered to the fullest possible extent. For the purpose of repressing the formation of meso-lactide, however, it is necessary that the reaction distillation be carried out at a relatively low temperature (180° to 200° C.). For the sake of effective discharge of the crude lactide vapor from the reaction part at such a low temperature, it is necessary that the reaction part be kept under a reduced pressure of not more than 20 mmHg, preferably not more than 10 mmHg. Under these conditions, though the amount of meso-lactide to be formed is decreased, the amount of lactic acid monomer to be formed is increased and the amount of lactide to be produced is decreased. Further, when the area available for the vaporization of the crude lactide from the reaction part is not sufficient in comparison with the volume of reaction, the velocity of the formation of lactide is determined by the rate of distillation and, as a result, the decomposition and racemization of lactide in the reaction solution is promoted and the amount of meso-lactide to be formed is increased. Thus, the scale-up production aimed at is not easily attained even by lowering the temperature and reducing the pressure. Further, it is not easy to repress the pressure loss in the zone ranging from the reaction part through the part for collection of the crude lactide below 20 mmHg, preferably below 10 mmHg.

The methods of reaction for the synthesis of optically active lactide from the prepolymer heretofore invented for the sake of solving the problems mentioned above include, for example, a method which comprises feeding such an inert gas as nitrogen gas to the reaction part for the synthesis of lactide and effecting the expulsion by distillation of the crude lactide under in the neighborhood of normal pressure as disclosed in WO 91/17155 and a method which comprises continuously feeding the prepolymer into a thin-film type reaction vessel and carrying out the reaction distillation at an elevated temperature for a short time as disclosed in WO 93/02075. These methods are invariably at a disadvantage in necessitating a voluminous and complicated apparatus.

The fact that the restrictions concerning the formation of meso-lactide in the reaction distillation part for the synthesis of optically active lactide are eliminated and the conditions for the operation of the reaction distillation part are allowed to be freely selected by adopting the method of this invention for the purification of lactide is extremely significant.

When the reaction distillation is carried out by the use of an ordinary kettle provided with a stirrer as the reaction vessel and the pressure of the reaction part is set at a level in the approximate range of 20 to 40 mmHg, the temperature in the reaction part is required to exceed 220° C. for ensuring thorough expulsion by distillation of the crude lactide. Though these conditions are easily accomplished from the industrial point of view, the amount of meso-lactide to be occurred in the crude lactic reaches a level in the approximate range of 1/10 to 1/3 of the amount of the optically active lactide. The production of lactide of sufficiently high optical purity from the crude lactide of this quality has been easily attained exclusively by the method of this invention for the first time.

As means to decrease the lactic acid monomer content in the crude lactide and improve the yield of lactide, the idea of heightening the molecular weight of the prepolymer as an intermediate may be conceived. Under these conditions, since the retention time in the reaction part is elongated, the reaction entails racemization and results in the formation of meso-lactide in a relatively large amount. Here again, the adoption of the method of this invention permits easy removal of meso-lactide and, as a result, enables the heretofore difficult production of lactide of high optical purity as a whole in a high yield to be realized.

Incidentally, in cases where DL-lactide is to be produced, the hydrolyzed meso-lactide may be recovered in conjunction with other acid components and reused as the raw material. In the case of the production of optically active lactide, however, the reuse as the raw material forms a cause for impairment of the optical activity. Thus, the recovered meso-lactide may be fully hydrolyzed and converted into lactic acid and the lactic acid so produced may be used as ordinary lactic acid.

Now, this invention will be described more specifically below with reference to working examples.

Example 1—Purification of DL-lactide

In a flask provided with a stirrer, 900 g (9 mols) of an aqueous 90 wt % DL-lactic acid solution was placed and, with 3.6 g of SnO added as a catalyst thereto, set thermally dehydrating while allowing the internal pressure of the flask to be reduced gradually so heedfully as to preclude expulsion by distillation of the lactic acid monomer together with water, and eventually subjected to continuous dehydration at 160° C. under 20 mmHg for one hour to synthesize a prepolymer. The molecular weight of this prepolymer was 1,200.

Then, the prepolymer produced in the flask was moved into a three-neck flask 2 of a test apparatus constructed as illustrated in FIG. 1. By the use of an external vacuum pump, the flask 2 was evacuated via a line 9 communicating with the vacuum pump to a reduced pressure of 20 mmHg and kept under this reduced pressure and, meanwhile, the prepolymer in the flask was stirred with a stirring rod 3 provided with the flask 2 and gradually heated by means of a mantle heater 1. Eventually, the prepolymer in the state ensuing on the preceding heat treatment was kept at 220° C. (the scale reading of a thermometer 4 provided with the flask 2) in order for crude lactide to be vaporized and expelled through the medium of a column 5 packed with Raschig rings (occasionally having a cord heater wound thereon as occasion demands) and an air-cooled tube 7 (occasionally having a cord heater wound thereon as occasion demands) and collected in a receptacle 8. In this while, the receptacle 8 was set in an oil bath 10 kept at a temperature of about 80° C. so as to prevent the crude lactide from solidifying. A thermometer 6 was set in the top part of the column 5 packed with Raschig rings and used to determine whether or not the column 5 packed with Raschig rings brought about cooling reflux of a low boiling distillate. The reaction distillation was substantially completed in three hours. The yield of the crude lactide thus produced was 620 g. The composition thereof was as shown in Table 3 below.

TABLE 3

| Composition of crude lactide | Composition ratio (wt %) |
| --- | --- |
| DL-lactide | 55.8 |
| Meso-lactide | 30.7 |
| Lactic acid monomer | 3.8 |
| Lactic acid dimer | 9.3 |
| Water | 0.4 |

Then, 600 g of the crude lactide in the molten state was mixed as kept stirred with 300 g of water of about 25° C. and the resultant solution was immediately immersed in an ice bath to be cooled wholly to about 25° C. within five minutes, and thereafter stirred continuously at room temperature for one hour. Immediately after this mixing, the mixture separated DL-lactide and assumed a slurry state.

Subsequently, the slurry was filtered centrifugally to separate DL-lactide crystals. When the separated DL-lactide crystals were dried at 40° C. under a reduced pressure, the total weight thereof was 307 g and the composition thereof was as shown in Table 4 below.

TABLE 4

| Composition of purified DL-lactide | Composition ratio (wt %) |
| --- | --- |
| DL-lactide | 95.0 |
| Meso-lactide | 2.5 |
| Lactic acid monomer | 1.0 |
| Lactic acid dimer | 1.4 |
| Water | 0.1 |

Then, 200 g of the DL-lactide was dissolved in 200 g of acetone at 56° C. and cooled as kept stirred to be recrystallized therein and kept at 20° C. for one hour. The crystals were separated by centrifugal filtration and dried at 40° C. under a reduced pressure. The yield of DL-lactide thus produced was 136 g and the composition thereof was as shown in Table 5 below.

TABLE 5

| Composition of repurified lactide | Composition ratio (wt %) |
| --- | --- |
| DL-lactide | 99.8 |
| Meso-lactide | 0.2 |
| Lactic acid monomer | Not detected |
| Lactic acid dimer | 0.02 |
| Water | 0.03 |

Example 2—Purification of DL-lactide

Crude lactide was obtained by reaction distillation effected by following the procedure of Example 1. The yield of crude lactide consequently obtained was 608 g and the composition thereof was as shown in Table 6 below.

TABLE 6

| Composition of crude lactide | Composition ratio (wt %) |
| --- | --- |
| DL-lactide | 54.5 |
| Meso-lactide | 31.3 |
| Lactic acid monomer | 3.1 |
| Lactic acid dimer | 8.3 |

TABLE 6-continued

| Composition of crude lactide | Composition ratio (wt %) |
|---|---|
| Water | 0.8 |

Then, 500 g of the crude lactide in the molten state was left cooling slowly while kept stirred to 60° C. Consequently, it separated DL-lactide crystals and assumed a slurry state.

Then, it was mixed as kept stirred with 250 g of water of about 25° C. and the resultant mixture was immediately immersed in an ice bath and cooled wholly to about 25° C. and thereafter stirred continuously at room temperature for 20 minutes.

Then, the slurry was centrifugally filtered to separate DL-lactide crystals. The separated DL-lactide crystals were dried at 40° C. under a reduced pressure. The total weight of the dried crystals was 261 g and the composition thereof was as shown in Table 7 below.

TABLE 7

| Composition of purified DL-lactide | Composition ratio (wt %) |
|---|---|
| DL-lactide | 95.5 |
| Meso-lactide | 2.2 |
| Lactic acid monomer | 0.8 |
| Lactic acid dimer | 1.2 |
| Water | 0.3 |

Example 3—Purification of L-lactide

In a flask provided with a stirrer, 900 g (9 mols, optical purity 99.5%) of an aqueous 90 wt % L-lactic acid solution was placed and, with 3.6 g of SnO added as a catalyst thereto, set thermally dehydrating while allowing the internal pressure of the flask to be reduced gradually so heedfully as to preclude expulsion by distillation of the lactic acid monomer together with water, and eventually subjected to continuous dehydration at 160° C. under 20 mmHg for one hour to synthesize a prepolymer.

Then, the prepolymer produced in the flask was moved into a flask 2 of an apparatus constructed as illustrated in FIG. 1. The prepolymer was brought to a reduced pressure of 7 mmHg and gradually heated and finally kept at 200° C. in order for crude lactide to be expelled by distillation and collected in the receptacle 8. The receptacle 8 was set in an oil bath kept at about 90° C. for the purpose of preventing the crude lactide from solidifying. The reaction distillation was substantially completed in three hours. The yield of crude lactide thus produced was 598 g. The composition thereof was as shown in Table 8 below.

TABLE 8

| Composition of crude lactide | Composition ratio (wt %) |
|---|---|
| D + L-lactide[1] | 88.5 |
| Meso-lactide | 3.0 |
| Lactic acid monomer | 4.3 |
| Lactic acid dimer | 3.6 |
| Water | 0.6 |
| Optical purity (%) | 97.5 |

[1]D + L-lactide = D-lactide + L-lactide
Composition ratio of D + L-lactide

TABLE 8-continued

| Composition of crude lactide | Composition ratio (wt %) |
|---|---|

Total composition ratios of those of D-lactide and L-lactide
The term "D + L-lactide" is used herein similarly in Tables 9 to 20.

Then, 500 g of the crude lactide in the molten state was mixed as kept stirred with 500 g of water of about 25° C. The resultant mixture was immediately immersed in an ice bath and cooled wholly to about 25° C. within five minutes and subsequently stirred continuously at room temperature for one hour. Immediately after the mixing, the mixture separated L-lactide and assumed a slurry state.

Then, the slurry was centrifugally filtered to separate L-lactide crystals. The separated L-lactide crystals were dried at 40° C. under a reduced pressure. The weight of the dried crystals consequently produced was 380 g and the composition thereof was as shown in Table 9 below.

TABLE 9

| Composition of purified L-lactide | Composition ratio (wt %) |
|---|---|
| D + L-lactide | 98.9 |
| Meso-lactide | 0.5 |
| Lactic acid monomer | 0.2 |
| Lactic acid dimer | 0.3 |
| Water | 0.1 |

Then, 350 g of this L-lactide was dissolved in 175 g of acetone at 56° C. The resultant solution was cooled as kept stirred to induce separation of crystals and kept at 20° C. for one hour. The crystals were separated by centrifugal filtration and dried at 40° C. under a reduced pressure. The yield of L-lactide consequently obtained was 245 g and the composition thereof was as shown in Table 10 below.

TABLE 10

| Composition of repurified L-lactide | Composition ratio (wt %) |
|---|---|
| D + L-lactide | 99.8 |
| Meso-lactide | Not detected |
| Lactic acid monomer | Not detected |
| Lactic acid dimer | 0.02 |
| Water | 0.03 |

The mother liquid which remained after the separation by filtration of crystals produced in the acetone solution was concentrated at 50° C. under a reduced pressure, cooled as kept stirred to induce separation of remaining lactide in the form of crystals. Consequently, 94 g of crude lactide was obtained. The crude lactide was dissolved in 47 g of acetone at 56° C. The resultant solution was cooled as kept stirred to induce separation of crystals and kept at 20° C. for one hour. The crystals were separated by centrifugal filtration and dried at 40° C. under a reduced pressure. The yield of L-lactide produced consequently was 57 g and the composition thereof was as shown in Table 11 below.

TABLE 11

| Composition of purified L-lactide | Composition ratio (wt %) |
|---|---|
| D + L-lactide | 99.97 |
| Meso-lactide | Not detected |

TABLE 11-continued

| Composition of purified L-lactide | Composition ratio (wt %) |
|---|---|
| Lactic acid monomer | Not detected |
| Lactic acid dimer | 0.01 |
| Water | 0.02 |

Example 4—Purification of L-lactide From Raw Material Having High Meso-lactide Content In a flask provided with a stirrer, 900 g (9 mols, optical purity 99.5%) of an aqueous 90 wt % L-lactic acid solution was placed and, with 3.6 g of SnO added as a catalyst thereto, set thermally dehydrating while allowing the internal pressure of the flask to be reduced gradually so heedfully as to preclude expulsion by distillation of the lactic acid monomer together with water, and eventually subjected to continuous dehydration at 160° C. under 20 mmHg for one hour to synthesize a prepolymer.

Then, the prepolymer produced in the flask was moved into a flask 2 of an apparatus constructed as illustrated in FIG. 1. The prepolymer was brought to a reduced pressure of 30 mmHg and gradually heated and finally kept at 220° C. in order for crude lactide to be expelled by distillation and collected in the receptacle 8. The receptacle 8 was set in an oil bath kept at about 90° C. for the purpose of preventing the crude lactide from solidifying. The reaction distillation was substantially completed in two hours. The yield of crude lactide thus produced was 459 g. The composition thereof was as shown in Table 12 below.

TABLE 12

| Composition of crude lactide | Composition ratio (wt %) |
|---|---|
| D + L-lactide | 72.1 |
| Meso-lactide | 18.1 |
| Lactic acid monomer | 1.6 |
| Lactic acid dimer | 5.4 |
| Water | 2.7 |
| Optical purity (%) | 87.1 |

Then, 400 g of the crude lactide in the molten state was mixed as kept stirred with 400 g of water of about 25° C. and the resultant solution was immediately immersed in an ice bath to be cooled wholly to about 25° C. within five minutes, and thereafter stirred continuously at room temperature for one hour. Immediately after this mixing, the mixture separated L-lactide and assumed a slurry state.

Subsequently, the resultant slurry was filtered centrifugally to separate L-lactide crystals. When the separated L-lactide crystals were dried at 40° C. under a reduced pressure, the total weight thereof was 265 g and the composition thereof was as shown in Table 13 below.

TABLE 13

| Composition of purified L-lactide | Composition ratio (wt %) |
|---|---|
| D + L-lactide | 97.1 |
| Meso-lactide | 2.1 |
| Lactic acid monomer | 0.3 |
| Lactic acid dimer | 0.2 |
| Water | 0.3 |

Then, 200 g of this L-lactide was dissolved in 100 g of acetone at 56° C. The resultant solution was cooled as kept stirred to induce separation of crystals and kept at 20° C. for one hour. The crystals were separated by centrifugal filtration and dried at 40° C. under a reduced pressure. The yield of L-lactide consequently produced was 127 g and the composition thereof was as shown in Table 14 below.

TABLE 14

| Composition of repurified L-lactide | Composition ratio (wt %) |
|---|---|
| D + L-lactide | 99.5 |
| Meso-lactide | 0.3 |
| Lactic acid monomer | Not detected |
| Lactic acid dimer | 0.01 |
| Water | 0.01 |

Example 5—Purification of L-lactide Using Prepolymer With High Molecular Weight

In a flask provided with a stirrer, 900 g (9 mols, optical purity 99.5%) of an aqueous 90 wt % L-lactic acid solution was placed and, with 3.6 g of SnO added as a catalyst thereto, set thermally dehydrating while allowing the internal pressure of the flask to be reduced gradually so heedfully as to preclude expulsion by distillation of the lactic acid monomer together with water, and eventually subjected to continuous dehydration at 160° C. under 10 mmHg for two hours to synthesize a prepolymer. The molecular weight of this prepolymer was 2,070.

Then, the prepolymer was subjected to reaction distillation for 4.5 hours in the same manner as in Example 4. The yield of crude lactide consequently obtained was 493 g and the composition thereof was as shown in Table 15 below.

TABLE 15

| Composition of crude lactide | Composition ratio (wt %) |
|---|---|
| D + L-lactide | 79.3 |
| Meso-lactide | 19.2 |
| Lactic acid monomer | 0.2 |
| Lactic acid dimer | 0.3 |
| Water | 1.0 |

Then, 400 g of the crude lactide in the molten state was mixed as kept stirred with 400 g of water of about 25° C. and the resultant solution was immediately immersed in an ice bath to be cooled wholly to about 25° C. within five minutes, and thereafter stirred continuously at room temperature for one hour. Immediately after this mixing, the mixture separated L-lactide and assumed a slurry state.

Subsequently, the slurry was filtered centrifugally to separate L-lactide crystals. When the separated L-lactide crystals were dried at 40° C. under a reduced pressure, the composition thereof was as shown in Table 16 below.

TABLE 16

| Composition of purified L-lactide | Composition ratio (wt %) |
|---|---|
| D + L-lactide | 96.9 |
| Meso-lactide | 2.2 |
| Lactic acid monomer | 0.1 |
| Lactic acid dimer | 0.4 |

TABLE 16-continued

| Composition of purified L-lactide | Composition ratio (wt %) |
|---|---|
| Water | 0.4 |

Example 6—Purification of L-lactide On Commercial Scale

In a reaction kettle having an inner volume of 3 kl and provided with a stirrer, 1.8 tons of an aqueous 90 wt % L-lactic acid solution (optical purity 99.5%) and 7.3 kg of SnO as a catalyst were placed, heated under a reduced pressure for three hours and allowed to reach at a temperature of 160° C. and to a reduced pressure of 100 mmHg, and left aging under these conditions for one hour and further for one hour under a reduced pressure of 20 mmHg. The amount of water to be removed consequently was about 500 kg. Then, the reaction mixture was gradually heated to remove the crude lactide by distillation. In about 30 minutes after the start of the heating with the first 15 minutes omitted as the initial distillation, the reaction mixture was subjected to about three hours' reaction distillation at 220° C. under a pressure in the range of 30 to 50 mmHg to collect 1,050 kg of molten crude lactide in a receptacle kept at 90° C. The composition of the molten crude lactide was as shown in Table 17 below.

TABLE 17

| Composition of molten crude lactide | Composition ratio (wt %) |
|---|---|
| D + L-lactide | 71.5 |
| Meso-lactide | 20.0 |
| Lactic acid monomer | 2.0 |
| Lactic acid dimer | 6.0 |
| Water | 0.5 |

Then, 80 to 100 kg of the molten crude lactide was transferred into another container and stirred therein with 100 kg of water of 20° C. added thereto. The resultant mixture was immediately cooled to 20° C., kept at this temperature for about one hour, and centrifuged to separate the produced crystals. The crystals thus produced were dried at 40° C. under 20 mmHg. The composition of the dried crystals was as shown in Table 18 below.

TABLE 18

| Composition of crude lactide | Composition ratio (wt %) |
|---|---|
| D + L-lactide | 97.5 |
| Meso-lactide | 1.5 |
| Lactic acid monomer | 0.2 |
| Lactic acid dimer | 0.3 |
| Water | 0.5 |

The whole crude lactide obtained by the reaction distillation (containing about 690 kg of crystals) was treated similarly. The crystals consequently obtained was dissolved in 350 kg of acetone at 55° C. and cooled over a period of about two hours to 22° C. to induce separation therein of L-lactide in the form of crystals. The crystals were separated by centrifugal filtration. The crystals were dried at 40° C. under 20 mmHg. The yield of L-lactide crystals thus produced was 464 kg and the composition thereof was as shown in Table 19 below.

TABLE 19

| Composition of purified L-lactide | Composition ratio (wt %) |
|---|---|
| D + L-lactide | 99.7 |
| Meso-lactide | 0.2 |
| Lactic acid monomer | Not detected |
| Lactic acid dimer | 0.01 |
| Water | 0.01 |

The mother liquid which remained after separation by filtration of the crystals from the acetone solution was concentrated and cooled to obtain 190 kg of crystals. The crystals were redissolved in acetone and similarly treated. As a result, 124 kg of L-lactide crystals were obtained. The composition of the L-lactide crystals was as shown below.

TABLE 20

| Composition of repurified L-lactide | Composition ratio (wt %) |
|---|---|
| D + L-lactide | 99.5 |
| Meso-lactide | 0.3 |
| Lactic acid monomer | Not detected |
| Lactic acid dimer | 0.01 |
| Water | 0.01 |

What is claimed is:

1. A method for the purification of lactide characterized by removing meso-lactide from a mixture containing at least one lactide selected from the group consisting of L-lactide and D-lactide together with meso-lactide by causing said mixture to contact with water and separating the non-meso-lactide crystals.

2. A method for the purification of lactide characterized by removing meso-lactide from a mixture containing at least one lactide selected from the group consisting of L-lactide and D-lactide together with meso-lactide and existing in a molten state and, at the same time, inducing separation in the form of crystals of at least one lactide selected from the group consisting of L-lactide and D-lactide by causing said mixture to contact with water and separating the non-meso-lactide crystals.

3. A method for the purification of lactide characterized by removing meso-lactide from a mixture containing at least one lactide selected from the group consisting of L-lactide and D-lactide together with meso-lactide and at least partly existing in a molten state and, at the same time, inducing separation in the form of crystals of at least one lactide selected from the group consisting of L-lactide and D-lactide by causing said mixture to contact with water and separating the non-meso-lactide crystals.

4. A method according to any of claims 1 to 3, wherein the mixture containing at least one lactide selected from the group consisting of L-lactide and D-lactide together with meso-lactide contains lactic acid, water, and other impurities.

5. A method for the purification of lactide characterized by dissolving the crystals of at least one lactide selected from the group consisting of L-lactide and D-lactide obtained by the method set forth in any of claims 1 to 3 in a solvent incapable of reacting with said lactide and subjecting the resultant solution to recrystallization.

6. A method for the purification of lactide characterized by dissolving the crystals of at least one lactide selected from the group consisting of L-lactide and D-lactide obtained by the method set forth in claim 4 in a solvent incapable of reacting with said lactide and subjecting the resultant solution to recrystallization.

* * * * *